US008541760B2

(12) United States Patent
Gonschor

(10) Patent No.: US 8,541,760 B2
(45) Date of Patent: Sep. 24, 2013

(54) METHOD FOR CALIBRATING A DEFLECTION UNIT IN A TIRF MICROSCOPE, TIRF MICROSCOPE, AND METHOD FOR OPERATING THE SAME

(75) Inventor: Mattias Gonschor, Gleichen (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 266 days.

(21) Appl. No.: 12/989,493

(22) PCT Filed: Apr. 25, 2009

(86) PCT No.: PCT/EP2009/003035
§ 371 (c)(1),
(2), (4) Date: Nov. 30, 2010

(87) PCT Pub. No.: WO2009/132810
PCT Pub. Date: Nov. 5, 2009

(65) Prior Publication Data
US 2011/0057093 A1 Mar. 10, 2011

(30) Foreign Application Priority Data
Apr. 30, 2008 (DE) .......................... 10 2008 021 577

(51) Int. Cl.
G01J 1/58 (2006.01)
G01J 3/30 (2006.01)
G01N 21/25 (2006.01)
G02B 21/06 (2006.01)

(52) U.S. Cl.
USPC ..................... 250/459.1; 250/458.1; 356/317; 356/318; 356/417; 359/385

(58) Field of Classification Search
USPC ................... 250/459.1, 458.1; 356/317, 318, 356/417; 359/385
See application file for complete search history.

(56) References Cited

U.S. PATENT DOCUMENTS

| 2004/0001253 | A1 | 1/2004 | Abe et al. |
| 2007/0097496 | A1* | 5/2007 | Ulrich et al. ................... 359/385 |
| 2007/0153373 | A1* | 7/2007 | Uhl ............................... 359/386 |
| 2010/0171946 | A1 | 7/2010 | Hecker |

FOREIGN PATENT DOCUMENTS

| DE | 3942514 A1 | 9/1990 |
| DE | 10356238 A1 | 7/2005 |

(Continued)

OTHER PUBLICATIONS

PCT, "Written Opinion of the International Searching Authority", International Application No. PCT/EP2009/003035, International Filing Date: Apr. 25, 2009, 6 pages.

(Continued)

Primary Examiner — David Porta
Assistant Examiner — Mindy Vu
(74) Attorney, Agent, or Firm — Hoffman Warnick LLC

(57) ABSTRACT

The invention relates to a method for calibrating a deflection unit in a TIRF microscope, by means of which an angle of incidence of excitation light onto a specimen is adjusted, wherein a setting of said deflection unit is adjusted such that the pertaining angle of incidence is definitely greater or definitely smaller than an anticipated critical angle for total reflection of the excitation light on a surface of a used specimen, the angle of incidence is scanned by varying the setting of said deflection unit in the direction of an anticipated critical angle, an intensity of an optical response of the used specimen elicited by the excitation light being measured for each setting of the deflection unit, the intensity of the optical response of the specimen used is measured at least for a number of settings of the deflection unit until the intensity of the optical response of the specimen used traverses a flank, and the setting of the deflection unit pertaining to the flank is stored as the setting for the critical angle for total reflection at the specimen used.

20 Claims, 4 Drawing Sheets

FOREIGN PATENT DOCUMENTS

| | | |
|---|---|---|
| DE | 10 2006 021 996 A1 | 2/2007 |
| EP | 1 524 491 A1 | 4/2005 |
| JP | 2003215462 A | 7/2003 |
| WO | 2005031429 A1 | 4/2005 |
| WO | WO 2006/048683 A1 | 5/2006 |
| WO | 2008125855 A1 | 10/2008 |

OTHER PUBLICATIONS

PCT, "International Search Report", International Application No. PCT/EP2009/003035, Completion Date Aug. 21, 2009, 6 pages.

Huang et al., "Surface Plasmon Resonance Imaging Using a High Numerical Aperture Microscope Objective", Analytical Chemistry, vol. 79, No. 7, pp. 2979-2983, Apr. 1, 2007.

Oheim et al., "Non-linear Evanescent-field Imaging", Journal of Physics D. Applied Physics, vol. 38, pp. R185-R197, Jan. 1, 2005.

Axelrod et al., "Total Internal Reflection Fluorescence", Annual Review of Biophysics and Bioengineering, Annual Reviews Inc., vol. 13, pp. 247-268, Jan. 1, 1984.

Alexander Rohrbach, "Observing Secretory Granules with a Multiangle Evanescent Wave Microscope", Biophysical Journal, vol. 78, pp. 2641-2654, May 1, 2000.

* cited by examiner

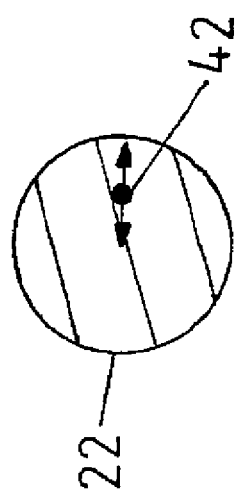
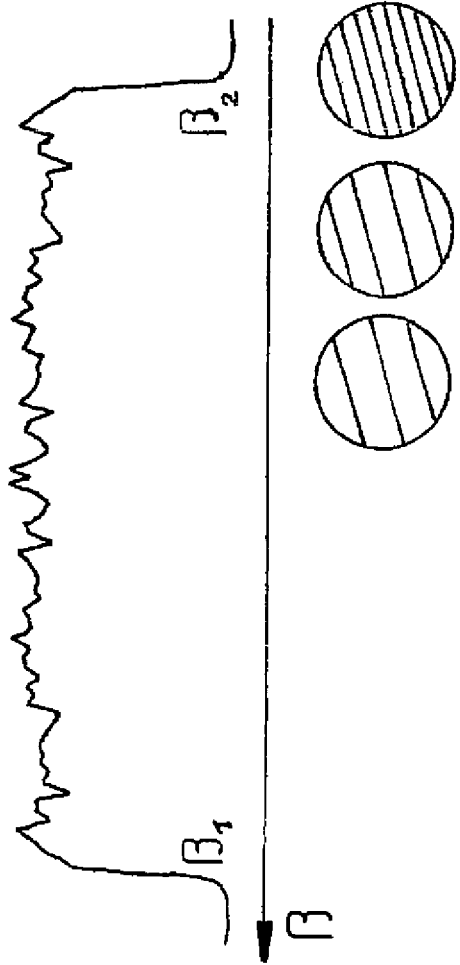

METHOD FOR CALIBRATING A DEFLECTION UNIT IN A TIRF MICROSCOPE, TIRF MICROSCOPE, AND METHOD FOR OPERATING THE SAME

FIELD OF THE INVENTION

In a first aspect, the invention relates to a method for calibrating a deflection unit in a TIRF microscope.

In a second aspect, the invention relates to a TIRF microscope.

In another aspect, the invention relates to a method for operating a TIRF microscope.

RELATED ART

In TIRF microscopy, it is important to be able to define precisely the angle at which the specimen is illuminated. With the help of this angle of incidence, it is possible to define other parameters of the evanescent field forming at the interface between a cover glass and a specimen as well as parameters of the specimen such as the penetration depth, refractive index, and critical angle for total reflection.

As a general rule, the angle of incidence is adjusted by means of a motor-driven deflection unit and influenced by the mechanical/optical manufacturing tolerances of the microscope components that are used, such as the filter set or the objective. For this reason, it is necessary to calibrate the deflection unit for each combination of components having different mechanical dimensions.

DE 10 2006 021 906 A1 describes a microscope for total internal reflection microscopy, wherein the illuminating light as well as the detection light are passed via the illuminating beam path through the objective and wherein at the interface to a specimen or specimen cover, preferably totally reflected illuminating light returns into the illuminating beam path. This reflected light is decoupled from the illuminating beam path and detected by a spatially resolving detector. Parameters of the evanescent field are then computed from the detected reflected light.

The hardware required for the method described therein is very complex. Along with complicated optics for decoupling the reflected light from the illuminating beam path, the method proposed in DE 10 2006 021 906 A1 merely uses totally reflected light, which thus carries only system-specific information but no specimen-specific information. This is problematic, since the angle for total reflection in particular and other parameters of the evanescent field depend on the refractive index of the specimen used.

SUMMARY OF THE INVENTION

It is an object of the invention to provide a method and to create a TIRF microscope with which a deflection unit in a TIRF microscope can be more precisely calibrated than in the prior art and other essential parameters of the evanescent field in a specimen can be determined.

Advantageous variants of the method of the invention and preferred embodiments of the TIRF microscope of the invention are the subject matter of the dependent claims.

In the method of the invention for calibrating a deflection unit in a TIRF microscope, with which an angle of incidence of excitation light onto a specimen is adjusted, a setting of the deflection unit is adjusted such that the associated angle of incidence is definitely greater or definitely smaller than an anticipated critical angle for the total reflection of the excitation light on a surface of a used specimen. The angle of incidence is then scanned by varying the setting of the deflection unit in the direction of an anticipated critical angle, wherein an intensity of an optical response of the specimen used elicited by the excitation light is measured for each setting of the deflection unit. The intensity of the optical response of the specimen used is measured at least for such a number of settings of the deflector unit until the intensity of the optical response of the specimen used traverses a flank, and the setting of the deflection unit pertaining to the flank is stored as a setting for the critical angle of the total reflection on the specimen used.

As a rule, a laser source is used as excitation light. However, use may also be made of other kinds of excitation light, such as standard mercury arc lamps.

The term "setting of the deflection unit" can be understood to mean an angular adjustment or alternatively some other kind of adjustment, such as a lateral adjustment of the deflection unit.

In a preferred variant of the invention, the intensity measurement can take place integrally via the objective pupil or a plane conjugated in relation thereto. The objective pupil is understood herein to mean the focal plane of the objective remote from the specimen.

In a preferred variant of the invention, for the purpose of scanning the angle of incidence of the excitation light, the setting of the deflection unit is automatically varied so that the focal point of the excitation light is once moved transversely across the entire objective pupil. In this variant, the excitation light is focused onto a point in the objective pupil. Since the latter is the focal plane of the objective remote from the specimen, the bundle of rays converging at this point is projected onto the specimen side as a parallel light beam which strikes the specimen at a specific angle of incidence that is identical for all rays. The location of the focal point of the excitation light or of the excitation bundle of rays in the objective pupil thus defines the angle at which the specimen is being illuminated. If the point in the objective pupil is scanned transversely across the center of the objective pupil, the angle of incidence of the excitation light thus changes from a large positive angle of incidence to perpendicular incidence and then to a large negative angle of incidence.

In the case of punctiform pupil illumination, all rays of the parallel bundle of rays strike the specimen at the same spatial angle.

In the case of a circularly annular pupil illumination, in which each ray is spaced at an identical distance from the central optical axis, each ray strikes the specimen at the same angle relative to the specimen, but the individual rays incident on the specimen are not parallel to one another. However, the bundle of rays exhibits a cylindrical symmetry.

A considerable advantage of the method of the invention is that the original TIRF objective and the original excitation filter set can be used.

Furthermore, the biological specimen itself can be used for calibration. No special test compound is needed. Furthermore, it is not necessary to know the refractive index of the specimen.

It is additionally advantageous that the analysis is very consistent. The entire camera image as well as portions of the pupil image can be analyzed.

Another advantage of the method of the invention is that the system is self-calibrating. Unlike the method disclosed in DE 10 2006 021 996 A1, no calibrated detector element is needed.

The TIRF microscope of the invention for carrying out the method of the invention has the following components: a light source for emitting the excitation light, a microscope objective for guiding the excitation light onto the specimen used, a deflector unit for adjusting the angle of incidence of the excitation light onto the surface of the specimen used, and a detector for detecting the optical response of the specimen used. The detector used can be a camera chip, e.g., a CCD, a photomultiplier, a PSD, photodiodes, or similar light detecting devices.

In the preliminary work that led to the invention, it was found that a calibration of a TIRF microscope using the light directly emitted by a specimen rather than the light reflected by the optics possesses considerable advantages.

The implementation of the intensity emitted by the specimen itself for calibrating a TIRF microscope can therefore be viewed as a basic concept of the invention. The parameters of the evanescent field can thus be determined with considerably greater accuracy than hitherto.

Furthermore, the solution of the invention requires only a very slight additional hardware effort. In particularly advantageous variants, only one supplementary lens is needed in order to achieve the invention.

According to the invention, use is made of the fact that upon reaching and exceeding the critical angle for total reflection, the penetration depth of the excitation light into the specimen decreases rapidly and then only equals a few 10 to 100 nm. The consequence thereof is that the background fluorescence coming from specimen portions that are more remote from the cover glass diminishes rapidly.

The expression "optical response" should be understood to mean a reaction of the specimen used to external excitation by light. In this case, the excitation light should not be limited to visible light, in particular infrared and ultraviolet light can be included. The reaction of the specimen used to such an excitation can likewise be diverse. The excitation light can either be scattered or else absorbed and then re-emitted. "Optical response" should in this case be understood to mean any type of luminescent radiation, particularly fluorescent radiation. In general, "optical response" should be understood to mean any radiation reaction of the specimen to light excitation.

To calibrate the deflection unit, the latter is adjusted so that the associated angle of incidence is definitely greater or definitely smaller than an anticipated critical angle for total reflection. Afterwards, the angle of incidence is varied in the direction of an anticipated critical angle and the intensity emitted by the specimen is at the same time measured. The flank then passed through is measured and analyzed. The same method is carried out in the case of punctiform pupil illumination of the TIRF objective for the second critical angle for total reflection, which differs from the first critical angle for total reflection only in terms of its sign. The zero adjustment of the deflection unit, also referred to as the angular offset, can then be ascertained from the flanks of the angle-dependent intensity gradient and the associated settings of the deflection unit.

This makes it possible to calibrate the deflection unit in absolute term, since the structurally dependent transfer function, which gives the angle of incidence as a function of the setting of the deflection unit, is known. It is not necessary to know the refractive index of the specimen in this case.

There is only one intensity flank available in systems that utilize an annular objective pupil illumination. In such systems, it is necessary to know the refractive index of the specimen to obtain an absolutely graded calibration. This can be achieved, for example, with the aid of a calibration compound having a known refractive index. Accordingly, with this arrangement the specimen to be examined cannot be used for calibration, as the refractive index of the specimen is generally unknown.

The critical angle for total reflection is expressed by the following relationship:

$$n_p = n_d \sin \alpha_T$$

Following the calibration of the deflection unit, and if the refraction indices of the specimen and the cover glass in the case of total reflection are known, the penetration depth d of the evanescent field can be adjusted using the angle of incidence α according to the following mathematical relationship:

$$d = \frac{\lambda}{4\pi \cdot n_d \sqrt{\sin^2\alpha - \sin^2\alpha_T}}$$

The penetration depth d is understood to mean the length in the direction of the optical axis, starting from the interface between the specimen and the cover glass, at which the intensity of the evanescent field in the specimen has faded to the $e^{th}$ fraction corresponding to a value of approx. 0.37 of the intensity of the light field at the interface.

In a preferred variant of the method of the invention, the optical response of the specimen used is measured in a plane conjugated to the plane of an objective pupil. Since the objective pupil is a common pass-through area for all light cones of the optical image, the objective pupil is particularly well-suited for measuring the optical response of the specimen. This is equivalent to measuring the optical response in a plane conjugated in relation to the objective pupil.

Particular preference is given to measuring the optical response with a detector, particularly by means of a camera. In this case, it is particularly advantageous to make use of the camera used in the TIRF measurement mode. It is then not necessary to switch cameras when switching from the measurement mode to the calibration mode and vice versa.

In another preferred variant, only sub-areas of a camera detector are used for analyzing the intensity. For example, the objective pupil can be projected onto the camera detector by imaging optics, and by means of a special software-controlled readout technology, only sub-areas of the camera detector can be selected for use in the analysis.

Particular preference herein is given to analyzing a sector of a circle that is only slightly larger than the image of the likewise circular objective pupil. However, use can be made of circular portions of the objective pupil image, or of rectangular portions that encompass a semicircle of the objective pupil image.

A particular advantage of this method is that the signal-to-noise ratio and the measurement speed can be greatly improved by selective analysis by the camera detector. The portions of such a camera image used for analysis purposes are also known as "regions of interest."

For speeding up the calibration procedure, preference is further given to scanning, by varying the angle of incidence, only in the vicinity of the anticipated critical angles or of an anticipated critical angle. Since, in practice, the zero point adjustment $\beta_0$ of the deflector unit, which corresponds to an angle of incidence of 0°, does not exceed a maximum value $\beta_{0max}$ specified by the individual tolerances, the positions of the anticipated critical angles for total reflection are already known to a certain degree. In view of this fact, scanning can be started immediately in a vicinity of an anticipated critical angle. This advantageously leads to a significant acceleration of the calibration procedure.

Additional acceleration can be achieved by operating the camera at a reduced resolution. As a general rule, this is achieved by interconnecting intensities of adjacent image elements, also known as binning. The image resolution is reduced in proportion to the number of grouped pixels. As a result, it is possible to proceed to the next measurement point at a greater speed during scanning. Another advantage resides in the fact that, with reduced resolution, the sensitivity of the camera increases and hence it is possible to use less illumination light for illuminating the specimen. This eases the stress on the specimen.

This method is suitable both for calibrating the system and for determining the calculation index for a series of different specimens.

In another particularly preferred variant, for punctiform pupil illumination, a first setting $\beta_1$ of the deflection unit is defined for a positive critical angle for total reflection and a second setting $\beta_2$ of the deflection unit is defined for a negative critical angle for total reflection, and the midpoint between the first setting $\beta_1$ and the second setting $\beta_2$ is defined as a zero adjustment $\beta_0$ of the deflection unit for perpendicular incidence of the excitation light onto the surface of the specimen used.

This method describes the actual calibration of the deflection unit when a punctiform pupil illumination is employed. This case is important, as it is the one most frequently encountered in practice. In this case, the light impinges on the specimen at a specific angle, which is equally large for all rays. From the settings of the deflection unit for both of the critical angles for total reflection, the midpoint for total reflection is determined, which corresponds to an incidence angle of 0° or a zero point adjustment $\beta_0$. An absolute angle calibration is then possible with the aid of the construction dependent transfer function.

Alternatively, the optical response of the specimen used can be measured in a plane conjugated in relation to the plane of the surface of the specimen used.

According to the invention, there are several methods for calibrating the setting of the deflector unit. The critical angles for total reflection and the calculation index of the specimen can be determined therefrom.

When employing a punctiform objective pupil illumination, absolute calibration of the scale is thus possible. This means that a fixed relationship between the setting of the deflection unit and the absolute magnitude of the angle of incidence has been established. Furthermore, the absolute value of the critical angle for total reflection $\alpha_T$, of the refractive index of the specimen $n_p$, and the zero point adjustment $\beta_0$ for perpendicular incidence can be determined from the curve of the measured intensity. For this purpose it is necessary to know how far the setting of the deflection unit must be adjusted in order to change the angle of incidence $\alpha$ to a specific extent. This is given by the construction dependent transfer function. Provided this is the case, it is possible to determine the absolute value of the angle of incidence for total reflection, by means of which the calculation index of the specimen $n_p$ can be determined.

In another advantageous embodiment of the method of the invention, when employing for a punctiform pupil illumination and when utilizing the calculation indices of the specimen used and of a cover glass and after defining the settings of the critical angle for total reflection, it is particularly preferred to assign absolute values of the angle of incidence uniquely to the settings of the deflection unit.

In another variant of the method of the invention, for circularly annular pupil illumination and when utilizing the calculation indices of the specimen used and of the cover glass and after defining the setting of the critical angle for total reflection, absolute values of the angle of incidence are uniquely assigned to the settings of the deflection unit.

A preferred embodiment of the TIRF microscope of the invention has supplementary optics capable of being revolved into a projection beam path for switching between the imaging of the specimen used and an imaging of an objective pupil on the detector. Thus, in this simple manner it is thus possible to switch between the TIRF measurement mode, in which the specimen is reproduced on a detector, and the TIRF calibration mode, in which the objective pupil is reproduced on the detector by means of the supplementary optics. This can be achieved, for example, by the use of a supplementary optics switching mechanism in a camera adapter.

In this embodiment, particular preference is given to the use of the camera that is also used in the TIRF measurement mode as a detector. Hence it is not necessary to change the detector when switching between a TIRF measurement mode and a TIRF calibration mode, and use can be made of one and the same camera.

Alternatively, a separate detector can be provided for measuring the optical response. Under certain circumstances, it is advantageous in the TIRF calibration mode to use a separate detector, such as a photomultiplier or semiconductor detector, rather than to use the same camera used in the TIRF measurement mode.

The method of the invention for operating a TIRF microscope is carried out using a TIRF microscope of the invention. In doing so, the deflector unit is calibrated according to the method of the invention and the angle of incidence of the excitation light is set to a value that is greater in magnitude than a critical angle for total reflection, following which TIRF measurements are carried out.

Accordingly, the deflection unit is first calibrated by means of the method of the invention. The zero point adjustment $\beta_0$ of the deflection unit corresponding to an angle of incidence of 0° and the absolute value of the critical angle for total reflection $\alpha_T$ can thus be determined. Subsequently, the angle of incidence of the excitation light is adjusted to a value that is greater in magnitude than the critical angle for total reflection. In this range, an evanescent field then forms in the specimen behind the interface between the cover glass and the specimen, which excites specimen particles in this interface. TIRF measurements are then carried out in this configuration.

Since it is desirable, in the case of total reflection, for the user to be able to adjust the penetration depth of the evanescent field continuously within a certain range, provision is made, according to another variant of the invention, for setting the associated angle of incidence $\alpha$ for a desired penetration depth d of the evanescent field on the basis of the following mathematical relationship:

$$d = \frac{\lambda}{4\pi\sqrt{n_d^2 \sin^2\alpha - n_p^2}}$$

wherein $\lambda$ designates the wavelength used, $n_d$ the calculation index of the cover glass, $n_p$ the calculation index of the specimen, and $\alpha$ the angle of incidence of excitation light relative to the specimen. This formula for the penetration depth d is equivalent to the aforementioned relationship for d. This can be verified by simply substituting according to the equation: $n_p = n_d \sin\alpha_T$.

An evanescent field no longer exists if $\alpha$ is smaller than the critical angle for total reflection $\alpha_T$. Instead, the incident ray is refracted and propagates through the specimen. Theoretically, an infinitely large penetration depth arises for the critical case in which the angle of incidence is equal to the critical angle for total reflection $\alpha_T$. This penetration depth, however, rapidly diminishes for larger angles of incidence α. In practice, the penetration depth d lies within a range of some 10 to some 100 nm. By means of the aforementioned relationship, the user can adjust the penetration depth d very precisely using the method of the invention, which is particularly advantageous for TIRF measurements.

In another preferred variant of the method of the invention for operating a TIRF microscope, the critical angle for total reflection is determined for a specimen used, and the calculation index of the specimen used is determined by implementing the critical angle for total reflection and also the calculation index of the cover glass.

This method can be used for rapid determination of the calculation index for a series of different specimens. As the calculation index of the cover glass used is generally known, the calculation index of the changed specimen can be easily deduced from the established critical angle for total reflection.

BRIEF DESCRIPTION OF THE DRAWINGS

Other advantages and features of the methods of the invention and the device of the invention are explained below with reference to the diagrammatic figures, in which:

FIG. 4 is a diagrammatic illustration of the position of the focal point of the excitation light in the objective pupil; and FIG. 5 is a measurement curve of the integral intensity as a function of the setting β of the deflection unit and is an illustration of the light intensities in the objective pupil.

DETAILED DESCRIPTION OF THE INVENTION

Figure 1:
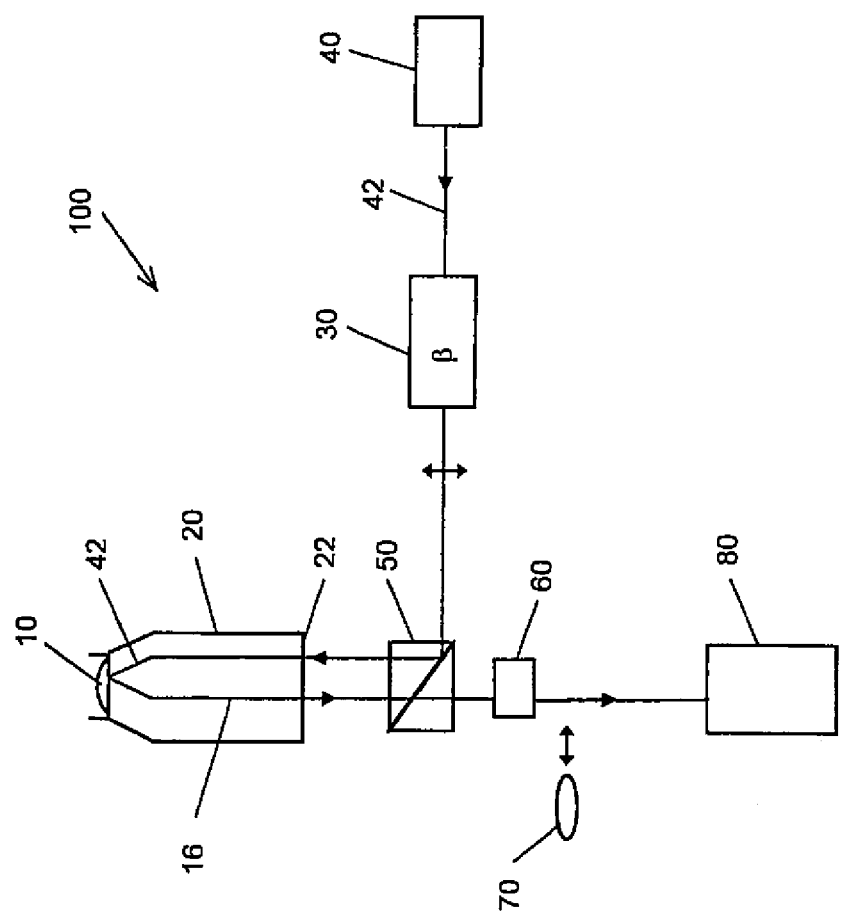
FIG. 1 is a diagrammatic view of an exemplary embodiment of a TIRF microscope of the invention.

The TIRF microscope 100 of the invention diagrammatically illustrated in FIG. 1 has the following components: a light source 40, a deflection unit 30, a microscope optics 20, a reflector module 50 as well as a supplementary optics 70, and a detector 80.

The excitation light 42 emitted by the light source 40 initially passes through the deflection unit 30, by means of which it is deflected to various extents depending on the setting R. The deflected excitation light 42 is diverted by the reflector module 50 toward a specimen 10 and passes firstly through the objective pupil 22 to enter the microscope optics 20, which guides the excitation light 42 onto the specimen 10. A light path in the microscope optics 20 is diagrammatically indicated in FIG. 1.

An optical response generated by the specimen 10, for example fluorescent light and/or scattered light 16, passes symmetrically to a surface normal 18 of the specimen 10 back through the microscope optics 20, leaves the latter through the objective pupil 22, and again strikes the deflector module 50. The fluorescent light and/or scattered light 16 passes through the reflector module 50 and is reproduced by means of imaging optics 60 on a detector 80. In the configuration illustrated in FIG. 1, the imaging optics 60 reproduce the specimen 10 sharply on the detector 80. TIRF measurements can be performed in this state. When the supplementary optics 70 are revolved into the projection beam path, the objective pupil 22 is reproduced sharply on the detector 80. The TIRF microscope 100 of the invention can then be calibrated in this configuration. In other embodiments, the revolvable supplementary optics 70 can also be disposed upstream of, or within, the imaging optics 60 rather than downstream of the imaging optics 60 as shown in FIG. 1. It is also possible for the supplementary optics 70 to be revolved into a additional projection beam path not illustrated in FIG. 1.

Figure 2:
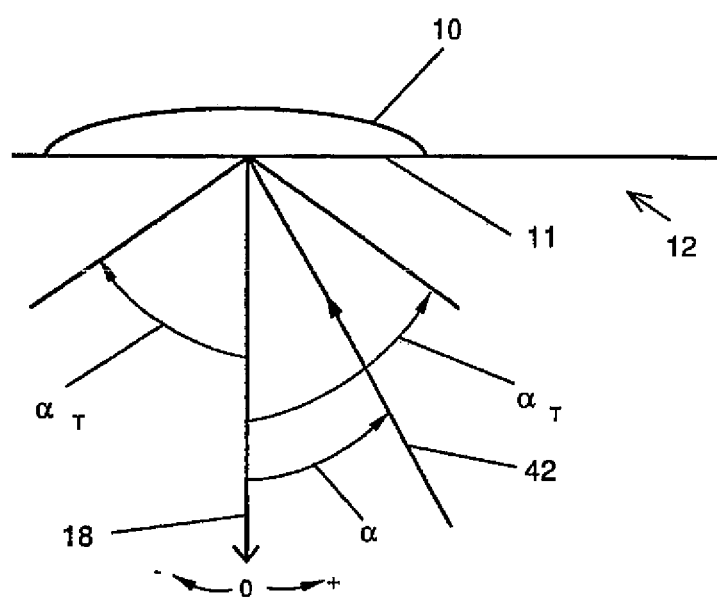
FIG. 2 is a diagrammatic illustration of the angle of incidence α and the critical angle for total reflection $\alpha_T$ on an interface between a cover glass and a specimen.

FIG. 2 diagrammatically illustrates how the angle of incidence α is measured at the interface 11 between a specimen 10 and a cover glass 12. A surface normal 18 is drawn in the direction of the cover glass 12 starting from the interface 11 between a specimen 10 and a cover glass 12. The angle between the incident excitation light 42 and the surface normal 18 is designated by α. By convention, here, angles plotted in the mathematically positive direction are designated as positive angles, while angles plotted in the mathematically negative direction are designated as negative angles. Also shown in the drawing are the two critical angles for total reflection $\alpha_T$ and $-\alpha_T$, which are plotted to the left and to the right of the surface normal 18 at the spacing of the critical angle for total reflection $$\alpha_T = \arcsin\left(\frac{n_d}{n_p}\right).$$

In an uncalibrated TIRF microscope, the angle of incidence α for zero point adjustment $\beta_0$ is generally not equal to 0°; hence there is an offset between the zero points of the α scale and of the β scale. This offset must be defined in order to calibrate the TIRF microscope.

Figure 3:
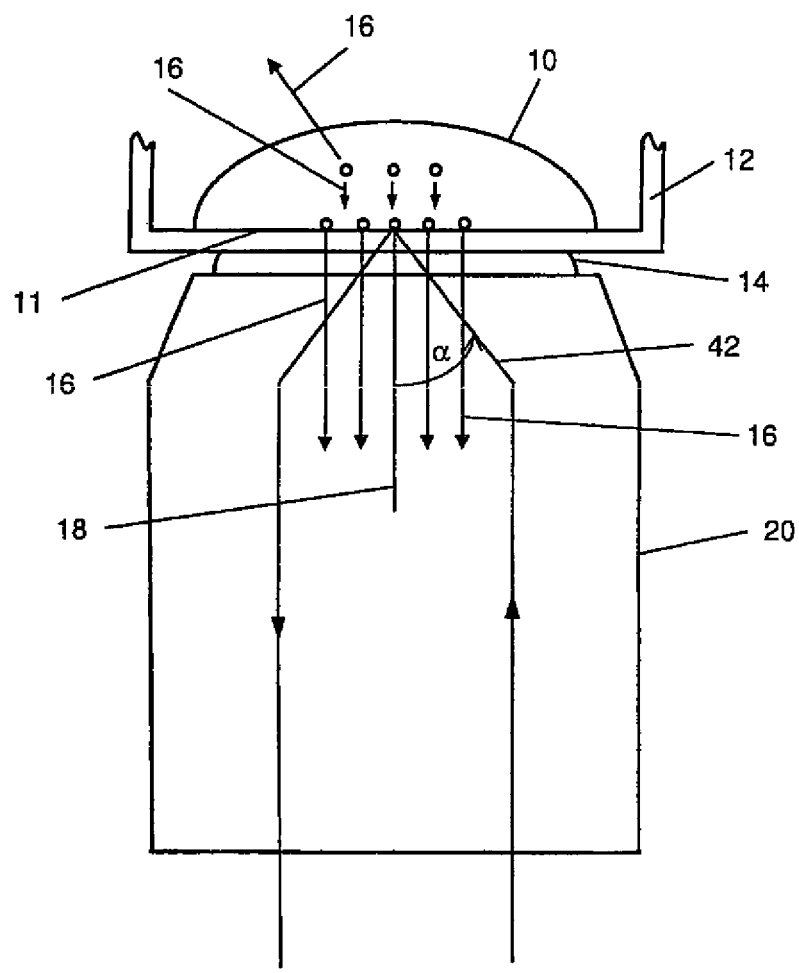
FIG. 3 is a diagrammatic partial view of an exemplary embodiment, in which, in particular, the specimen with cover glass, immersion oil, and an objective are illustrated.

FIG. 3 illustrates in greater detail the beam path within the microscope optics 20 and at the interface 11 between a specimen 10 and a cover glass 12. The excitation light 42 coming from the reflector module 50 is deflected through the microscope optics 20 such that it strikes the interface 11 between the specimen 10 and the cover glass 12 at an angle of incidence α.

As a general rule, a plurality of lenses is present in the microscope optics 20, at which the excitation light 42 is multiply refracted. These refractions are diagrammatically illustrated by a sharp bend in FIG. 3.

On leaving the microscope optics 20, the excitation light 42 enters an immersion oil 14. In the exemplary embodiment shown in this figure, the refractive index of the immersion oil 14 is equal to the refractive index of the cover glass 12 so that no refraction takes place at the interface between the immersion oil 14 and the cover glass 12.

When the angle of incidence α is larger than the total reflection angle $\alpha_T$, total reflection takes place at the interface 11 between the cover glass 12 and the specimen 10. An evanescent field typically extending some 10 to some 100 nm into the specimen 10 then forms on the specimen side behind the interface 11 between the cover glass 12 and the specimen 10. Diagrammatically indicated specimen particles emit fluorescent light 16 in all directions as an optical response. Since the evanescent field in the specimen 10 fades exponentially in the direction of the optical axis, the majority of the fluorescent light 16 is irradiated from specimen particles present near the interface 11 between the specimen 10 and the cover glass 12. The total light reflected by the interface 11 between the specimen 10 and the cover glass 12 passes symmetrically to the incident excitation light 42 on the other side of the surface normal 18 through the microscope optics 20 and leaves the latter via the objective pupil 22 in the direction of the reflector module 50.

FIG. 4 illustrates diagrammatically how the focal point of the excitation light 42 is displaced in the objective pupil 22. The angle of incidence α at the interface 11 between the specimen 10 and the cover glass 12 increases as a consequence when the distance between the center of the circle describing the objective pupil 22 and the focal point of the excitation light 42 passing through the plane of the objective pupil 22 increases.

FIG. 5 shows the intensity profile of the integrated intensity measured in the detector 80 as a function of the setting β of the deflector unit 30. According to the invention, the supplementary optics 70 is in this embodiment revolved into the projection beam path in order to make it possible to calibrate the TIRF microscope of the invention (see FIG. 1).

Images of the objective pupil, which correspond to the positions with the settings β of the deflector unit 30, are illustrated at the bottom of FIG. 5. The light intensity herein was measured in the objective pupil 22 or in a plane conjugated thereto.

The cross hatching symbolizes the intensity of the light 16 emitted from the specimen 10.

Two flanks or jumps in intensity corresponding to the two critical angles for total reflection $α_T$ can be discerned. The plateau-like zone between the two flanks corresponds to the cases in which no total reflection occurs, but instead, the excitation light 42 propagates farther through the specimen 10. Thus much scattered light or fluorescent light 16 is obtained from the volume of the specimen 10, which leads to a higher intensity in the objective pupil 20 or in a plane conjugated in relation thereto.

When the critical angle for total reflection $α_T$ coming from this zone is approached, the integral intensity drops sharply and reaches a minimum value when the critical angle for total reflection is exceeded. This can be discerned in the outer zones of the graph.

Upon reaching and exceeding the critical angle for total reflection $α_T$, an evanescent field, of which the penetration depth d decreases very rapidly as a function of the angle of incidence α forms behind the interface 11 in the specimen 10. This is illustrated by the images of the objective pupil at the bottom edge of FIG. 5. Since only a few specimen particles are henceforth able to emit light, the integral intensity is in this case much lower than in this case when total reflection has not yet occurred.

The setting $β_0$ of the deflection unit that corresponds to a specimen illumination angle α of 0° can be calculated from the position of the two flanks. This is expressed as follows:

$$β_0(α = 0°) = \frac{β_1 + β_2}{2}$$

In this case $β_1$ and $β_2$ are the settings of the deflection unit 30 that correspond to the critical angles for total reflection $α_T$. Accordingly, the signs of the angles $β_1$ and $β_2$ must be noted in order to calculate $β_0$ correctly.

On this basis, it is possible to adjust specific angles of incidence since, owing to the optical and mechanical configuration, the angle of incidence α and the setting β of the deflection unit 30 are in a fixed functional relationship to each other:

$$α=f(β-β_0), β=β_0+f^{-1}(α),$$

in which f describes a function and $f^{-1}$ describes an inverse function associated therewith. Since the function f is known in typical situations, it is only necessary to define a constant, for instance $β_0$ in the present case, in order to achieve an absolute calibration of the deflection unit 30.

Furthermore, if it is possible to calculate the absolute magnitude of the critical angle $α_T$ in the respective configuration, it will also be possible to effect absolute calibration of the setting β of the deflection unit 30. This means that an absolute value α can be assigned to each value β of the deflector unit. In this case the refractive index of the specimen $n_p$ can be calculated furthermore from one of the two critical angles $α_T$.

In the case in which the fluorescent filter set is present in the illumination beam path, a calibration of the deflection unit 30 should be performed for each combination of objective 20 and fluorescent filter set, as each of these individual components shows different dimensional deviations.

With circularly annular pupil illumination, the fact that here only one intensity flank is available must be taken into account. In this case the orientation of the circularly annular excitation light 42 in relation to the optical axis must be as accurately centered as possible, as otherwise the angle of incidence α would not be the same at all points on the circular ring. Assuming an accurate adjustment and provided that the grading of the scale is calibrated, it will be possible to determine the absolute value of the critical angle $α_T$ for total reflection. If the refractive index of the specimen 10 is also known, it will likewise be possible to carry out an absolute calibration of the deflection unit 30.

The present invention provides a novel method for calibrating a deflection unit in a TIRF microscope, a corresponding TIRF microscope, and also a method for operating such a TIRF microscope, with which it is possible to perform an exceptionally precise calibration of a TIRF microscope as well as a precise determination of a critical angle for total reflection with minimal additional hardware effort. This can be brought about with a less apparatus expense than in the prior art.

The invention claimed is:

1. A method for calibrating a deflection unit in a TIRF microscope, with which an angle of incidence of excitation light onto a specimen is adjusted, comprising:
    (a) adjusting a setting of the deflection unit such that a pertaining angle of incidence is greater or smaller than an anticipated critical angle for total reflection of an excitation light on a surface of a specimen;
    (b) scanning the angle of incidence by varying the setting of the deflection unit in a direction of the anticipated critical angle, and measuring an intensity of an optical response of a specimen elicited by the excitation light for each setting of the deflection unit;
    (c) measuring the intensity of the optical response of the specimen at least for a plurality of different settings of the deflection unit until the intensity of the optical response of the specimen traverses a flank; and
    (d) storing the setting of the deflection unit pertaining to the flank as the setting for the critical angle for total reflection at the specimen.

2. The method as defined in claim 1, wherein the optical response of the specimen is measured in a plane conjugated to a plane of an objective pupil.

3. The method as defined in claim 1, wherein the optical response is measured with a detector.

4. The method as defined in claim 1, wherein the optical response is measured with a camera.

5. The method as defined in claim 4, wherein the optical response is measured with a camera used in a TIRF measuring mode.

6. The method as defined in claim 4, wherein, for evaluation of the intensity, only subregions of a camera detector are used.

7. The method as defined in claim 4, wherein, for acceleration of the calibration of the angle of incidence, the camera is operated at a reduced resolution.

8. The method as defined in claim 1, wherein, for acceleration of a calibration of the angle of incidence, scanning is effected only in a vicinity of the anticipated critical angles or of an anticipated critical angle.

9. The method as defined in claim 1, wherein, to achieve a punctiform pupil illumination, a first setting of the deflection unit is determined for a positive critical angle for total reflection and a second setting of the deflection unit is determined for a negative critical angle for total reflection, and wherein the setting of the deflection unit for a vertical incidence of the excitation light onto the surface of the specimen is defined as a midpoint between the first setting and the second setting.

10. The method as defined in claim 1, wherein the optical response of the specimen is measured in a plane conjugated to a plane of the surface of the specimen.

11. The method as defined in claim 1, wherein, as optical response, at least one of a fluorescent light or a scattered light of the specimen is measured.

12. The method as defined in claim 1, wherein, to achieve a punctiform pupil illumination using refractive indices of the specimen and of a cover glass, and following determination of the settings of the critical angle for total reflection, unique absolute values for the angle of incidence are assigned to the settings of the deflection unit.

13. The method as defined in claim 1, wherein, to achieve a circularly annular pupil illumination utilizing refractive indices of the specimen and of the cover glass, and following determination of the setting of the critical angle for total reflection, unique absolute values for the angle of incidence are assigned to the settings of the deflection unit.

14. A method for operating a TIRF microscope, the TIRF microscope comprising a light source for the emission of excitation light; microscope optics for guiding the excitation light onto the specimen; a deflection unit for the adjustment of the angle of incidence of the excitation light on the surface of the specimen; a detector for detecting the optical response of the specimen; and supplementary optics, capable of being revolved into an optical imaging path, for switching between an imaging of the specimen and an imaging of an objective pupil on the detector;
wherein the deflection unit is calibrated by the method defined in claim 1, the angle of incidence of the excitation light is adjusted to a value, the magnitude of which is greater than a critical angle for total reflection, and TIRF measurements are then carried out.

15. The method as defined in claim 14, wherein on the basis of the mathematical relationship:

$$d = \frac{\lambda}{4\pi \cdot n_d \sqrt{\sin^2\alpha - \sin^2\alpha_T}}$$

in which
λ denotes a wavelength used,
$n_d$ denotes a refractive index of a cover glass,
α is the angle of incidence of the excitation light on the specimen, and
$\alpha_T$ is the critical angle for total reflection,
the associated angle of incidence is adjusted to reach a desired depth of penetration d of an evanescent field in the specimen.

16. The method as defined in claim 15, wherein the refractive index of the specimen is determined by utilizing the critical angle for total reflection and the refractive index of the cover glass.

17. A TIRF microscope, comprising:
a light source for the emission of excitation light;
microscope optics for guiding the excitation light onto the specimen;
a deflection unit for the adjustment of the angle of incidence of the excitation light on the surface of the specimen, wherein the deflection unit is configured for:
   adjusting a setting of the deflection unit such that a pertaining angle of incidence is greater or smaller than an anticipated critical angle for total reflection of an excitation light on a surface of a specimen;
   scanning the angle of incidence by varying the setting of the deflection unit in a direction of the anticipated critical angle, and measuring an intensity of an optical response of a specimen elicited by the excitation light for each setting of the deflection unit;
   measuring the intensity of the optical response of the specimen at least for a plurality of different settings of the deflection unit until the intensity of the optical response of the specimen traverses a flank; and
   storing the setting of the deflection unit pertaining to the flank as the setting for the critical angle for total reflection at the specimen;
a detector for detecting the optical response of the specimen; and
supplementary optics, capable of being revolved into an optical imaging path, for switching between an imaging of the specimen and an imaging of an objective pupil on the detector.

18. The TIRF microscope as defined in claim 17, wherein a separate detector is provided for measuring the optical response.

19. A TIRF microscope, comprising:
a light source for the emission of excitation light;
microscope optics for guiding the excitation light onto the specimen;
a deflection unit for the adjustment of the angle of incidence of the excitation light on the surface of the specimen, wherein the deflection unit is configured for:
   adjusting a setting of the deflection unit such that a pertaining angle of incidence is greater or smaller than an anticipated critical angle for total reflection of an excitation light on a surface of a specimen;
   scanning the angle of incidence by varying the setting of the deflection unit in a direction of the anticipated critical angle, and measuring an intensity of an optical response of a specimen elicited by the excitation light for each setting of the deflection unit;
   measuring the intensity of the optical response of the specimen at least for a plurality of different settings of the deflection unit until the intensity of the optical response of the specimen traverses a flank; and
   storing the setting of the deflection unit pertaining to the flank as the setting for the critical angle for total reflection at the specimen;
a detector for detecting the optical response of the specimen; and
a separate detector for measuring the optical response.

20. The TIRF microscope as defined in claim 19, further comprising:
supplementary optics, capable of being revolved into an optical imaging path, for switching between an imaging of the specimen and an imaging of an objective pupil on the detector.

* * * * *

UNITED STATES PATENT AND TRADEMARK OFFICE
CERTIFICATE OF CORRECTION

| | | |
|---|---|---|
| PATENT NO. | : 8,541,760 B2 | Page 1 of 1 |
| APPLICATION NO. | : 12/989493 | |
| DATED | : September 24, 2013 | |
| INVENTOR(S) | : Mattias Gonschor | |

It is certified that error appears in the above-identified patent and that said Letters Patent is hereby corrected as shown below:

On The Title Page, Item (73) Assignee
Assignee "Carl Zeiss MicroImaging GmbH" (full address: Carl Zeiss Promenade 10, Jena, Germany 07745) should be updated to "Carl Zeiss Microscopy GmbH" (full address: Carl-Zeiss-Promenade 10, Jena, Germany 07745)

Signed and Sealed this
Sixth Day of January, 2015

Michelle K. Lee
*Deputy Director of the United States Patent and Trademark Office*